United States Patent [19]
Ochoa et al.

[11] Patent Number: 5,716,358
[45] Date of Patent: Feb. 10, 1998

[54] DIRECTIONAL BONE FIXATION DEVICE

[75] Inventors: Jorge A. Ochoa, Norton; Laurel Rogers, North Attleboro, both of Mass.

[73] Assignee: Johnson & Johnson Professional, Inc., Raynham, Mass.

[21] Appl. No.: 348,607

[22] Filed: Dec. 2, 1994

[51] Int. Cl.⁶ .................................................. A61B 17/68
[52] U.S. Cl. .............................. 606/62; 606/60; 606/72; 606/73
[58] Field of Search .......................... 606/73, 72, 54, 606/59, 61, 62, 63, 64, 76

[56] References Cited

U.S. PATENT DOCUMENTS

| | | |
|---|---|---|
| 2,381,050 | 12/1945 | Hardinge . |
| 2,397,545 | 2/1946 | Hardinge . |
| 2,490,364 | 2/1949 | Livingston . |
| 2,699,774 | 5/1955 | Livingston . |
| 3,678,925 | 7/1972 | Fischer et al. . |
| 3,716,051 | 2/1973 | Fischer . |
| 3,782,374 | 1/1974 | Fischer . |
| 3,797,113 | 3/1974 | Brainin . |
| 3,805,775 | 4/1974 | Fischer et al. . |
| 3,849,887 | 11/1974 | Brainin . |
| 4,011,602 | 3/1977 | Rybicki et al. . |
| 4,355,428 | 10/1982 | Deloison et al. . |
| 4,592,346 | 6/1986 | Jurgutis . |
| 4,743,256 | 5/1988 | Brantigan ............................ 623/17 |
| 4,745,913 | 5/1988 | Castaman et al. . |
| 4,834,757 | 5/1989 | Brantigan ............................ 623/17 |
| 4,878,915 | 11/1989 | Brantigan ............................ 623/17 |
| 5,222,983 | 6/1993 | Schmitz et al. . |

FOREIGN PATENT DOCUMENTS

| | | |
|---|---|---|
| 2154272 | 3/1973 | Germany . |
| 2 115 701 | 9/1983 | United Kingdom . |
| WO-A-85 03857 | 9/1985 | WIPO . |

OTHER PUBLICATIONS

Bruce A. Banks, "Topography: Texturing Effects", pp. 338–361 in *Handbook of Ion Beam Processing Technology*, Cuomo et al. eds., Noyes Publications, Park Ridge, NJ (1989).

Bruce A. Banks, "Ion Bombardment Modification of Surfaces in Biomedical Applications", Chapter 10 (pp. 398–434) in *Ion Bombardment Modification of Surfaces*, Auciello et al. eds., Elsevier Publishers (1984).

*Primary Examiner*—Guy V. Tucker
*Attorney, Agent, or Firm*—Nutter, McClennen & Fish, LLP

[57] ABSTRACT

A bone fixation device such as a screw, pin, staple, cable or anchor has a microtextured contact surface to enhance installation or gripping characteristics, preferably by providing directional or anisotropic engagement. A surface texture comprised of patterned microfeatures imparts a roughness or actual mechanical engagement that prevents loosening. In different embodiments the features resemble an array of microbumps or pyramids, or anisotropic features such as rasp teeth, shingles, or slanted cantilevered fiber/rods. The use of microbumps present a smaller surface area when moving, while providing full area contact after the surfaces have relaxed or decompressed; installation may be effected with low force, while high static or resting friction prevents disengagement. Features with directional asymmetry or angled suspension allow the textured surface to slide or deflect when the fixation device moves in one direction, while presenting a high resistance to torque or linear motion when moved in the other direction. Manufacturing is achieved with ion beams or directional treatment with energetic radiation, and regular arrays of the microfeatures may be produced as stationary surface growth phenomena without the use of pattern masks or mechanical contact. One manufacturing apparatus rotates the fixation device about a longitudinal axis while it is irradiated along an oblique axis. A bone pin may have centrally-directed spurs that allow a multi-segment fracture to be securely pinned without threading. An elastic fastener body such as a screw or pin can be pre-tensioned to place the bone under a torsional or compressive load, or introduce strain at the healing site.

17 Claims, 5 Drawing Sheets

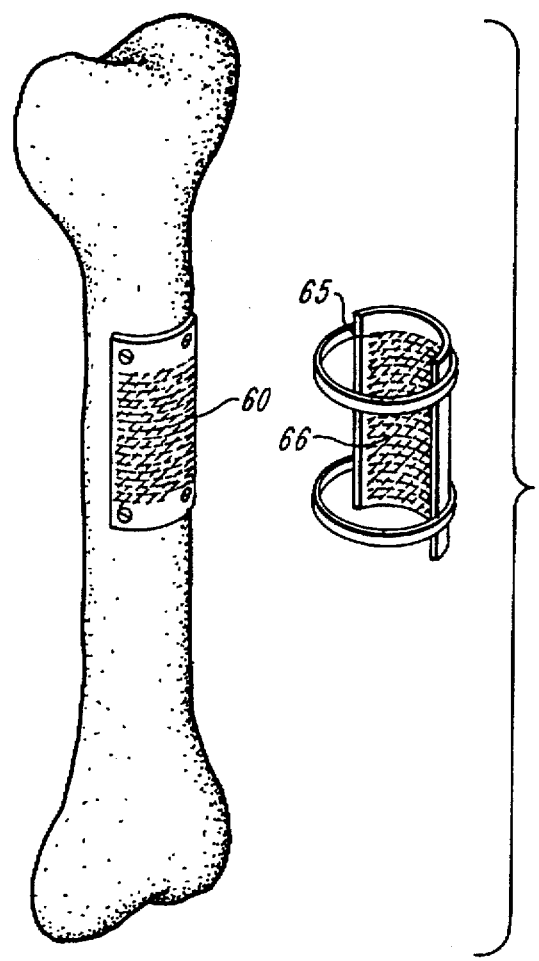
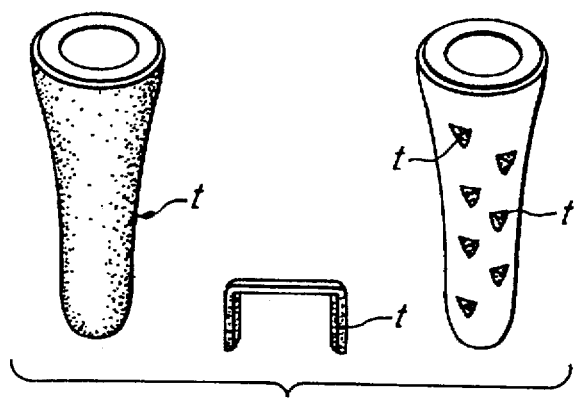

DIRECTIONAL BONE FIXATION DEVICE

BACKGROUND OF THE INVENTION

The present invention relates to mechanical fixation devices and hardware used in surgical applications to attach or anchor bone tissue or prosthetic devices to bone, or to secure pieces of bone together. Some examples of such devices are bone screws, bone pins, eye hooks and anchor assemblies. It is a common feature of these devices that they are fitted into a precisely drilled or reamed hole and they are intended to anchor firmly against one or more bone contacting surfaces. In particular, bone screws generally have extensive thread surfaces which cut or press against precut grooves in a hole drilled into a bone. Bone pins generally also similarly fit tightly against a hole wall, or have a bone engaging surface which allows them to fix at least one end of the pin. Fixation devices such as eye hooks may also be fastened to bone to allow suturing of soft tissue such as muscle, tendon or connective to a particular spot on the bone.

In general, these bone fixation devices have mechanical aspects analogous to those of the corresponding conventional fastening elements such as pins, screws, anchors and the like. In this regard, their functioning is dictated largely by a body or rod of high tensile, shear and bending strength, a plurality of screw threads with a sufficient lateral surface area for great load bearing ability, and in some instances self-tapping or wedging properties, and other mechanical structures which are substantially identical to those of the corresponding general purpose screw, pin or the like. Surface texture has figured relatively little, if at all, in the construction of bone fastener hardware.

In some areas of the bone prosthesis field, surface texture has been found to be quite important. Thus, when replacing acetabular joints or structural endings for major bones, e.g., artificial knees or hips, it has previously been realized that the surface texture of the metal prosthesis may be tailored to be more or less conducive to the ingrowth of bone material and thus the formation of a strong cement-free bond to existing bone. Textures for this purpose have been formed in a cast metal bone prosthesis, for example, by brazing on additional small surface features such as balls, wires, or screens which collectively define protrusions and indentations into and about which bone may grow to form a relatively strong and shear resistant coupling. In certain circumstances, the presence of suitably textured surfaces on such prostheses may allow the surgeon to dispense with cement or other bonding materials which otherwise had been generally required to form at least a temporary bond to the prosthesis during the process of bone healing. The scale of surface patterning which has been found useful in bone attachment extends from what might be described as a macroroughness, with pores of approximately 100 microns and larger, to what might be described as a relatively jagged surface configuration with structures extending a millimeter or more outside the plane of the nominal prosthesis surface. As a rule, the utility of such features is related to their ability to support or encourage trabecular bone growth and the ultimate formation of a hard organic bond to the prosthesis.

On a different level, surface texturing such as knurling may be applied to symmetrical items such as bone pins to achieve an ultimate increase in the shear strength where they bond to a bone. Here, the relative feature size is again measured in fractions of a millimeter, and the bond-strengthening mechanism appears somewhat similar to that described for prosthetic bones in providing a network in which bone intergrowth may extend in a depth dimension to form a shear free interface. However, these designs for addressing the shear strength of the bone coupling layer address the relatively long term strength of the interface so formed; for such a design, the short term strength immediately following installation is not affected, and in fact, if installed without adhesive, the interface may be considerably more fragile due to the smaller direct and rigid contact area involved.

Also, items such as bone screws having a self-wedging taper may become loose quite quickly if they start to back off. Thus, care must always be exercised in fitting the bone fastener tightly enough without exerting such great force as to crack bone or risk subsequent loosening of the device.

Various structures have been developed for providing secure fixation, among which may be cited those of U.S. Pat. Nos. 2,381,050; 2,397,545; 2,490,364; 2,699,774; 3,678,925; 3,716,051; 3,782,374; 3,805,775; and 4,011,602; 4,355,428; 4,743,256; 4,745,913; 4,834,757 and 4,878,915. All of these structure address, to some extent, the provision of a mechanical gripping or biting mechanism that can be tightened sufficiently to provide a sure grip while limiting to some extent the magnitude of stresses created in the surrounding bone. This is generally done with protrusions that bite in localized regions, self-limiting wedging arrangements that distribute stress and provide only gradual expansion, porous or polymer mechanical contact faces, or combinations of these features. However, in general these fixation devices still rely on a screw-tightened wedging action, and often they provide a broad range of adjustment so that the correct feel or torque during installation to assure fixation without introducing destructive levels of strain is left to the mechanical skill, experience and judgment of the surgeon. Since the installation process itself necessarily generates debris that may create binding and provide a false sense of torquing into solid material, the success or longevity of installation may therefore involve some element of luck, even when performed by a highly experienced and meticulously careful surgeon.

Accordingly, there is a need for fixation devices that provide uniform and secure fixation characteristics.

There is also a need for bone fasteners having a mechanical design that offers improved tightening and holding ability, yet with less risk of creating high stresses in the bone to which they attach.

SUMMARY OF THE INVENTION

This is achieved in accordance with the present invention by providing a bone fastener having a bearing surface which contacts a bone or anchor to secure the fastener thereto, wherein a microscopic surface texture of the bearing surface provides directional holding power. The holding power is provided by a directional surface roughness which, for example, allows a screw or a pin to go into its securing opening more easily than it backs out. In various embodiments, this directional asymmetry is produced by forming a plurality of oriented microstructures on the surface. Suitable microstructures include columns, ridges, trenches, and the like. According to a preferred embodiment, the microstructures are produced by ion beam bombardment as stationary patterns, in a process wherein an ion beam or directional source of energetic particles acts on the surface of the fixation device, either with or without masking. Anisotropy of the pattern may be achieved by orienting an ion beam at an angle with respect to an active face of the fastener device so that a ripple-like or column or fuzzy surface microtexture is formed. The features have the effect of angled levers, or angled rasp teeth which bite or flex to resist movement in one direction and yet flex or slide to allow a relatively easy contact movement in the other direction. Isotropic patterns may also be used to provide a more uniform torque resistance as a function of compressive loading, with a lower constant of proportionality. Particular examples are shown for micro-features forming a directional surface roughness on the face of a screw, or the surface of a rod or pin.

BRIEF DESCRIPTION OF DRAWINGS

These and other features of the invention will be understood from the description below taken together with the following Figures, wherein:

FIG. 7 illustrates a two-part embodiment; and

FIG. 8 illustrates other fastener embodiments.

DETAILED DESCRIPTION OF THE DRAWINGS

Figure 1:
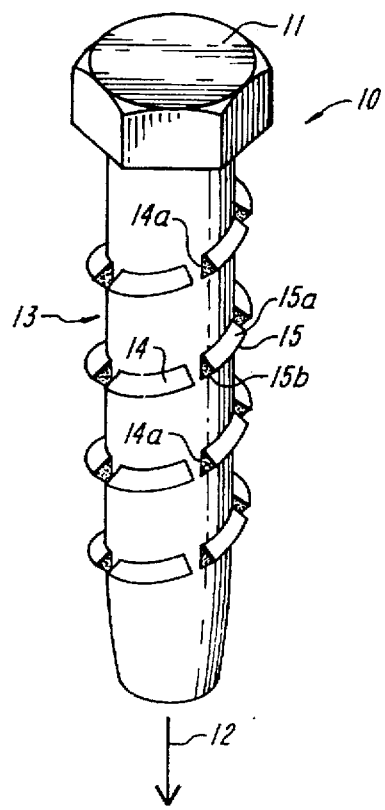
FIG. 1 shows a bone fixation screw in accordance with the present invention.

FIG. 1 illustrates the principles of the present invention in a bone screw 10, shown schematically. Screw 10 has a head 11 and a body 13, with the body 13 extending generally along a screw axis 12. A generally helical thread 14 winds along the length of the body. While a single continuous thread 14 is illustrated, plural parallel threads or interrupted thread segments may be employed as is known in the art. Thread segments, for example, may also have abrupt transverse faces 14a that define self tapping cutting edges for the thread profile. The thread is characterized by a pair of upper and lower laterally extending faces 15a, 15b which join at an apex 15, thus having a generally wedged-shaped cross section and an extended surface area in contact with the bone. Not uncommonly, each thread may be formed to extend further than the one that precedes it (i.e., the one that enters the bone ahead of it), either by extending radially further from the screw axis 12, or by having a wider wedge defined between the upper and lower bearing faces 15a, 15b lying above and below the peaked apex of the thread, so that as the screw advances each thread wedges somewhat in the space formerly occupied by the preceding thread. In accordance with the present invention, one of these contact surfaces 15a, 15b, or both has surface texture to provide a gripping engagement, preferably with a directional quality affecting bone engagement.

The general construction of screw threads is of course conventional, and the use of progressively sized thread surfaces, used for example in lag screws, provides a successively greater resistance as the screw is advanced so that it will lock firmly in position. It will be appreciated, however, that a conventional construction also results in the screw placing the bone in a highly stressed condition, with the result that a sharp impact might easily cause the bone to crack. Further, if a screw with progressive threads does back off even a little (for example, due to a cracked thread, or cracked bone surface contacting a thread), then the screw loosens entirely. Even when screws are not progressive, they must rely on a generally uniform wedging action, or simply on the large surface area of the threads and the axial component of force of the screw which is transmitted to the threads, to create a large static friction against these bearing faces and prevent rotation.

In either case, the action of the conventional screw against the brittle bone surface may result in substantial debris being created during initial insertion of the screw, and such debris may create binding or wedging during insertion which, although it feels like a solid attachment, may quickly disappear as pulverized material is resorbed, or further crushed. Thus, the mechanics of bone fixation devices of this type remains rather problematic as far as the general principles described above and it is this problem that the directional bearing surfaces of the present invention address.

The foregoing discussion of prior art aspects of the fixation device applies when the bone screw 10 is formed of a substantially smooth and strong hard stiff material. To a certain extent some problems of bone stress and breakage may be addressed by providing some surfaces of the fixation device made of a somewhat flexible and less stiff material such as a polyurethane, polyethylene or other biocompatible plastic. Thus, for example, plastic anchors may be used in a bone bore and the wedging action may occur against the plastic without imparting excessively localized destructive forces to the bone itself. In this case, the compliance of the plastic allows fitting with less risk of bone destruction, and the elasticity of the plastic also provides some assurance against abrupt loosening. The strength of plastic, however, is generally inadequate to secure fixation in load bearing applications, and plastic may be subject to cracking or other degradation over time.

The present invention approaches these problems by providing a microscopic surface texture on the bearing faces 15a, 15b of the fixation device. The surface texture is both smooth and of small magnitude so that it does not abrade the bone surface, and the texture extends outward from the surface so that the area of contact with bone is reduced, at least upon initial insertion. After insertion, when the bone has had an opportunity to relax or decompress and conform to the textured surface, a larger surface area contacts bone, making removal more difficult. Preferably, the surface texture itself is asymmetric or anisotropic, with angled features that facilitate installation, or discourage loosening. The asymmetry is selected to provide what may be called a directional roughness to the surface texture which allows the surface to slide freely into position and yet be quite difficult to back off or pull out of position. In this manner, insertion is possible without the creation of excessive stresses in the bone itself, and without risking destroying the underlying dimensions on which fixation depends.

Figure 2:
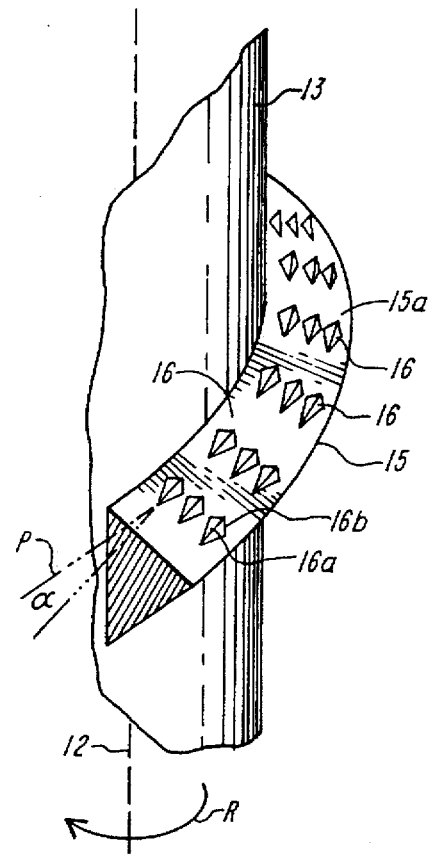
FIG. 2 shows a detail of directional surface microstructure in the screw of FIG. 1.

FIG. 2 illustrates one embodiment of a bone screw face having such a surface roughness. As illustrated, a thread 15a is shown winding counter-clockwise along a screw body 13. The thread surface 15a has a plurality of ridges 16 extending outward from the nominal plane of the face 15a and each ridge or mound 16 is asymmetric along the direction of contact motion experienced upon insertion. The illustrated thread is shown winding in a counter-clockwise direction along a pitch curve P, so that rotation in the clockwise sense indicated by arrow R advances the screw along the direction in which it points. Each of the ridges 16 is illustrated as having a front face 16a (that is, a face on the side which first contacts bone) which is narrowly sloped at an attack angle α to the pitch P, and a back face 16*b* which falls steeply down toward the surface 15*a*. This provides a texture, much like the scales of a fish or a shingled surface, wherein if one were to attempt to turn the screw in the direction opposite its direction of insertion, the bone face abutting face 15*a* would encounter relatively abrupt vertical edges 16*b* of the protrusions 16 and would therefore present a high degree of bite or resistance to turning. On the other hand, turning in the direction of rotation R presents a protrusion of very low slope angle, and thus poses relatively little resistance to turning. Typically, the protrusion 16 extends to a height above the surface 15*a* on the order of about one to about five hundred micrometers, preferably in the range of two to two hundred micrometers and most preferably about fifty to one hundred micrometers. The illustrated shape is rather similar to the shape, for example, of a sand dune, and like sand dunes, which are formed as a natural periodic or stationary feature under conditions of fluid stream, the features 16 may be formed at a steady state condition under certain forms of irradiation flux treatment. Despite their regularity, these patterns may be formed without requiring an extrinsic pattern mask or precisely controlling a discrete sculpting process.

In accordance with one aspect of the present invention, the features 16 are formed by ion beam bombardment of the screw 10 with an ion flux while the ion beam direction is controlled to provide the desired feature shape and orientation. For a general description of the processing technology involved in this aspect of the invention, reference is hereby made to the following publications which describe techniques of micropattern formation using ion beams: Bruce A Banks, *Topography: Texturing Effects* in *Handbook of Ion Beam Processing Technology*, Cuomo et al, eds. pp. 338–361 Noyes Publications, Park Ridge N.J. (1989). Bruce A. Banks: *Ion Bombardment Modification of Surfaces in Biomedical Applications*, chapter 10 in *Ion Bombardment Modification of Surfaces* Auciello et al, eds., pp. 399–434, Elsevier publications (1984). Each of these documents is hereby incorporated herein by reference for purposes of an informed guide to relevant technology and an indication of suitable processes and equipment for manufacturing the textured articles of the invention. A basic understanding of the invention is conveyed quite simply, however, by description of the feature size or orientation and the purpose these features achieve in bone fixation. Thus, the ridges or protrusions 16 are seen to be formed on the bearing faces 15*a*, 15*b* of the helical screw threads, and to cover a substantial area of the frictionally engaged surface of the screw. Their directionality is aligned with the direction of rotation of the thread such that motion along the insertion direction (clockwise in FIGS. 1 and 2) presents relatively little resistance, while motion in the reverse winding sense presents a high degree of frictional resistance. In the embodiment of FIG. 2, this is achieved by providing ripple-like surface contours of low overall height and having a low angle of the attack in the insertion winding rotational sense, and a high angle of attack in the unwinding sense.

Figure 3:
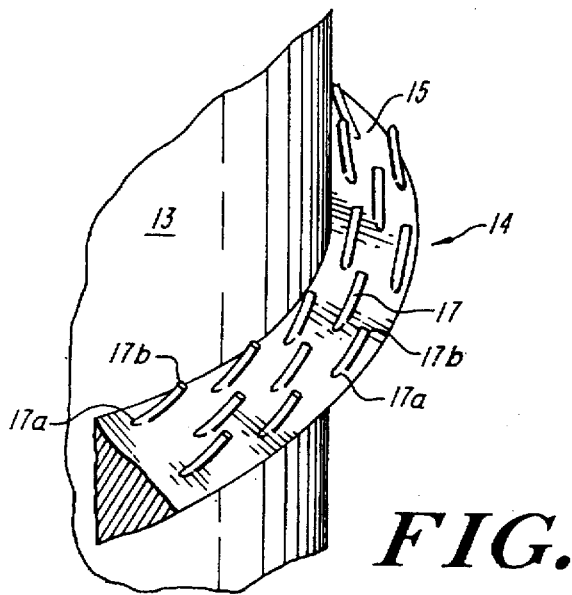
FIG. 3 shows an alternative embodiment of surface microstructure according to the present invention in a bone fastener.

FIG. 3 shows another surface microtexture suitable for achieving asymmetric directional gripping of a fixation device. In accordance with this aspect of the invention, an asymmetric microtexture is imparted by a plurality of oblique columns, fiber-like strands or beams 17 formed at the surface. Each strand 17 extends from the surface 18 upwardly and backwardly, with its front or base end 17*a* anchored firmly in the metal of the screw surface and its opposite free or extending end 17*b* pointing backwardly along the location path of the screw thread 14, 15. With this orientation, when the screw is advanced, the loose cantilevered or even flailing ends of the column/fibers 17 passively trail along, flexing in order to accommodate the abutting threaded edges in the bone opening in which the screw fits. However, if the screw starts to back off, the free end 17*b* of each column, rather than being dragged down flat against the screw face 15*a* as happens during insertion, is urged upwardly away from the face 15*a* and toward the adjacent bone surface in which the thread fits. When the end 17*b* of a column hits the bone surface, it grips, taking a high compressive force directed along its column or length, effectively locking the screw from turning in the backward direction. The mechanism here is somewhat analogous to that of short animal fur which presents a great stiffness or resistance when brushed the wrong way, yet can be quite smooth and frictionless brushed in the direction of its slant orientation.

As with the preceding micro-bump or ridge-like embodiment, the oblique trailing arms or columns 17 are preferably also formed by a process of ion beam bombardment of the screw thread face 15. In particular, for certain crystalline metals, the flexible elongated trailing arms may be formed by a mechanism commonly referred to as channeling wherein deep passages are eroded in a periodic fashion by the incoming ion beam. Channeling occurs in such crystal and metal forms, because sputter erosion preferentially occurs along planes extending into the surface aligned with weak crystal axes, leaving solid bodies intact along at least one dimension. Alternatively, the trailing column structure of FIG. 3 may be produced by methods involving ion beam bombardment through an appropriate microlithographic pattern mask. Manufacturing by this process involves placing a pattern defining mask, such as a carbon film mask patterned into a screen having a regular array of openings, over the area on which the pattern is to be formed and directing an ion beam obliquely through the mask at the surface. In general, regions not covered by the mask are sputtered away, while regions covered by the mask are protected as the mask erodes.

In the foregoing processes, the mask protects surface regions which are not to be textured. While the material forming the mask may itself also sputter, preferably the mask material or the process chamber atmosphere is selected to sputter and redeposit in a continuous way such that the mask itself does not suffer any substantial net erosion while sputtering of the unmasked portions proceeds. The unmasked portions being subject to a different dynamic in terms of relative sputtering rates and processes of redeposition, become textured or removed where they are exposed through apertures in the mask. For further details of this type of sputter patterning, including variations such as the use of additional ion beams, directed beams and reactive agents for defining special feature orientations and cleaning up sputtered material, reference is particularly made to the papers cited above.

Figure 4:
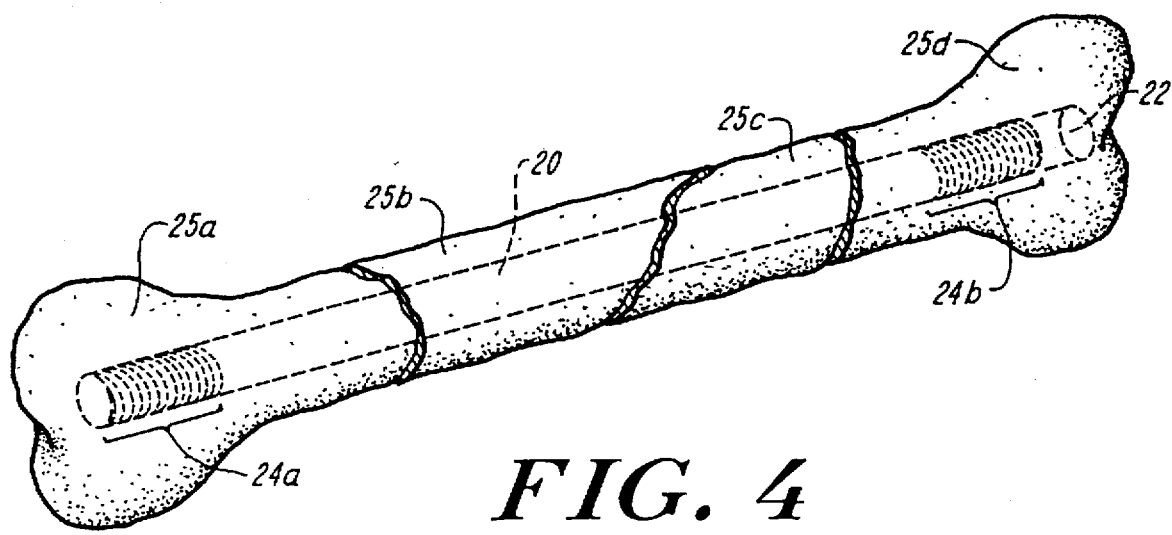
FIG. 4 shows a bone pin embodiment.

FIG. 4 shows another bone fixation device in accordance with the present invention. This device 20 is a bone pin illustrated in the position for threading a plurality of hollow bone fragments 25*a*, 25*b* . . . together. As shown, bone pin 20 is generally inserted by drilling or reaming out a precision bore 22 interiorly of bone 25 along its axial extent (when securing a fractured long bone), or in several massive fragments (when rejoining a fractured ball or bone end), and inserting the bone pin through the opening so formed. Generally, at least the end pieces of the broken bone so secured have openings which are sized to fit fairly exactly the diameter of the bone pin which may be, for example, threaded or textured in the corresponding regions 24a, 24b. As with the bone screw of FIG. 1, the pin of the present invention has a microtexture formed by ion beam treatment which makes removal of the pin difficult once it is inserted.

A preferred micropattern for this fixation device consists of the cantilevered or trailing columns 17 illustrated in FIG. 3. These columns are preferably oriented trailing along the direction of insertion so that they deflect inwardly like simple cantilevered spikes or beams as the pin is being inserted while they are urged radially outward and jam against the surrounding bone if the pin starts to move in its opposite direction. They thus operate in a sense like the barbs on a porcupine quill which make removal almost impossible. As with the microstructure formed on the bone screw 10, these columns are preferably formed by patterned ion beam bombardment with an oblique orientation of the ion beam with respect to the axis of the bone pin 20.

In general, the term bone pin as used herein is quite broad, encompassing elongated needle- or rod-like members that are inserted along an axial direction, and which may be either non-load bearing, or load bearing, in either an axial or transverse direction. At one extreme, a pin may be thin and elongated but relatively short, like a tack or nail, while at another extreme, as shown in FIG. 4, a pin may be a centimeter or more in diameter and ten, twenty or more centimeters long. Similarly, a pin may be entirely unbendable and inextensible, as a solid metal rod; may be formed of a somewhat bendable or extensible material such as a plastic rod or shaft; or may be quite flexible, like a rope or cable, made, for example of the same materials as sutures or suture clips and intended primarily to resist force or motion along its length. Pins may also be hollow for low weight, or may be composed of a combination of hollow bushings with an internal cable when necessary to provide axial force without unnecessary weight or rigidity. In this disclosure and the claims appended hereto, the term "pin" shall include all such meanings, although for clarity of exposition the Figures will use a simple rod or shaft as illustrative of the pin.

One embodiment of this aspect of the invention is a bone pin which essentially barbs "out" in opposite directions at its two ends to form a double-ended, oppositely-directed, directionally gripping pin that, when inserted in a bone, even without additional fixation devices such as nuts or anchors, will resist the bone pulling off of either end of the pin. This construction is analogous to a double-ended porcupine quill or doubled ended harpoon, and is achieved by irradiating with an ion beam as illustrated schematically in FIG. 6.

Figure 5:
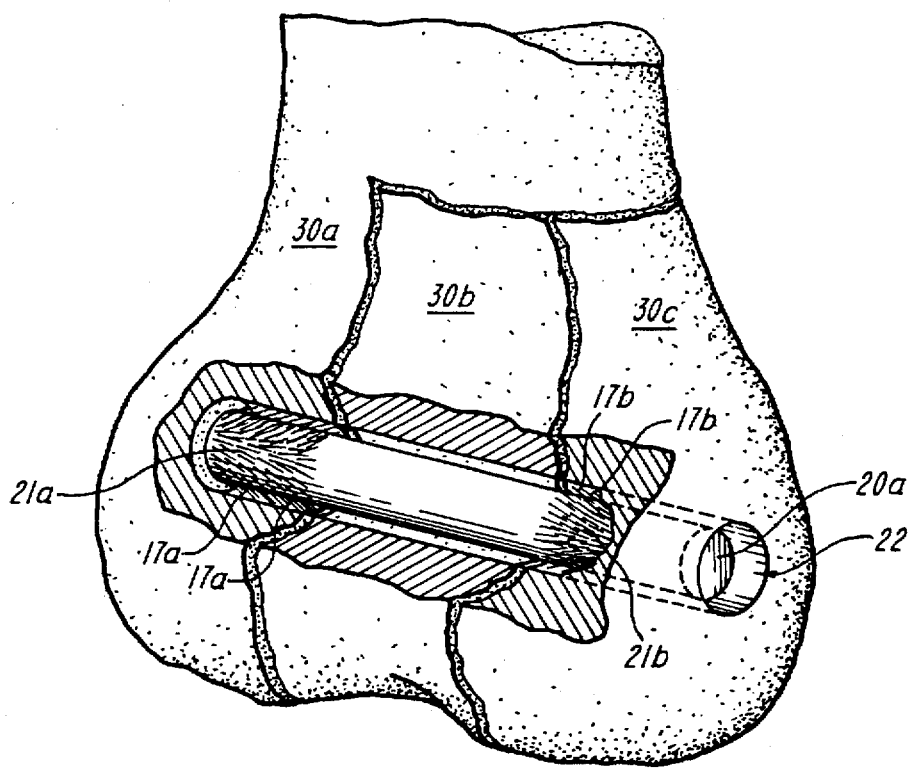
FIG. 5 shows another bone pin embodiment.

FIG. 5 illustrates bone fragments 30a, 30b and 30c secured together with such a bone pin 20a. The fragments are aligned together and a bore 22 drilled to secure their aligned orientation. Pin 20a has a distal end 21a having a first plurality of column-like gripping fibrils 17a, like the gripping texture elements 17 of FIG. 3, which fit into and secure the pin 20a in the distal bone segment 30a. As shown, fiber elements 17a point toward the center, and away from the distal end, of the pin, so that when the pin is inserted in the bone 22 in bone segment 30a, it will not slide out. The opposite (proximal) end of pin 20a has gripping columns 17b which point in the opposite direction, toward the distal end. With this directionality bone fragments 30b and 30c may be slideably positioned over the proximal end 21b of the pin, and once in position, the directional fibrils 17b prevent either the bone or pin from loosening outwardly. The middle section of the pin, between ends 21a, 21b may be untextured, or may have the texture of end 21a (if the pin is to be inserted into the bone fragment), or of end 21b (if the bone fragment is to be moved into position over the pin). In general, the nature of the fracture line will determine whether adjacent fragments must be positioned together before or after insertion of the pin.

For various fixation purposes, the number, diameter and length of the columns 17 may be determined empirically to assure that the pin installs without creating or becoming clogged with excessive debris, yet develops a strong resistance to slipping in the outward direction. It will be appreciated that the double-ended pin configuration allows the first end of the pin to be inserted with low insertion force into a distal bone fragment, as shown in FIG. 5, after which the remaining bone fragment is slipped onto the other end of the pin with a net movement of surfaces in the opposite sense. Thus, the subsequent fragment or fragments each is inserted along a direction of low insertion force. Once so reconstructed, neither end piece can move outwardly, at either end, and outward motion is subject to a much higher resisting force.

Figure 5A:
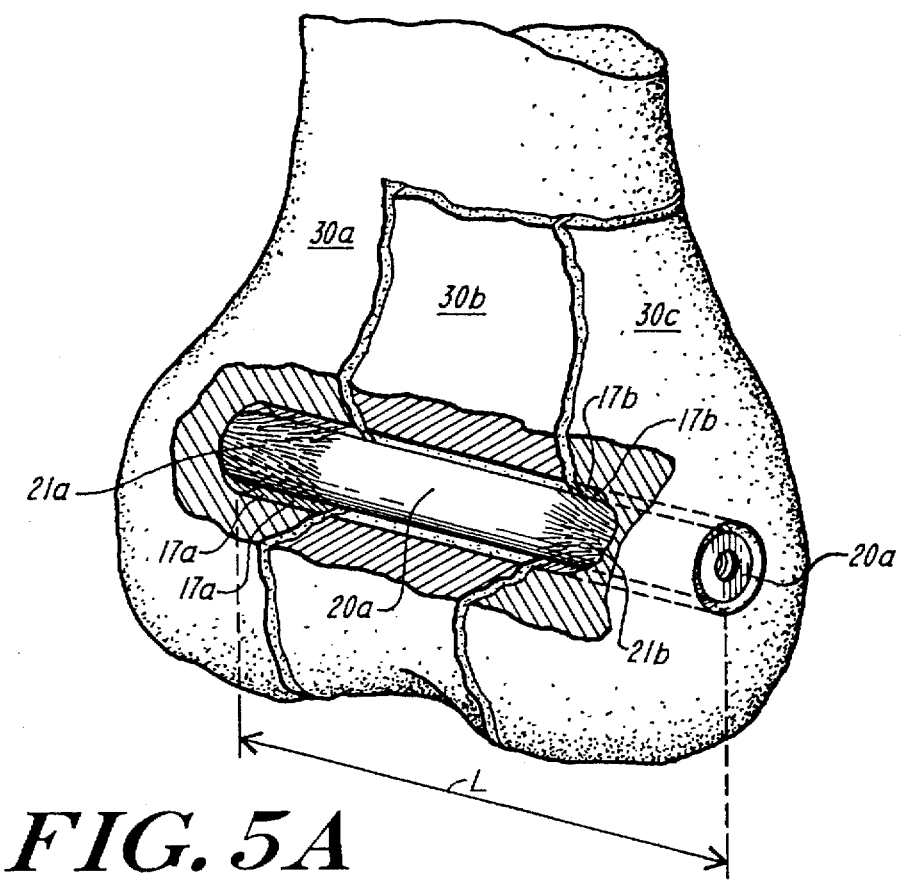
FIGS. 5A–5C illustrate a method of use of the bone pin of FIG. 5.
Figure 5B:
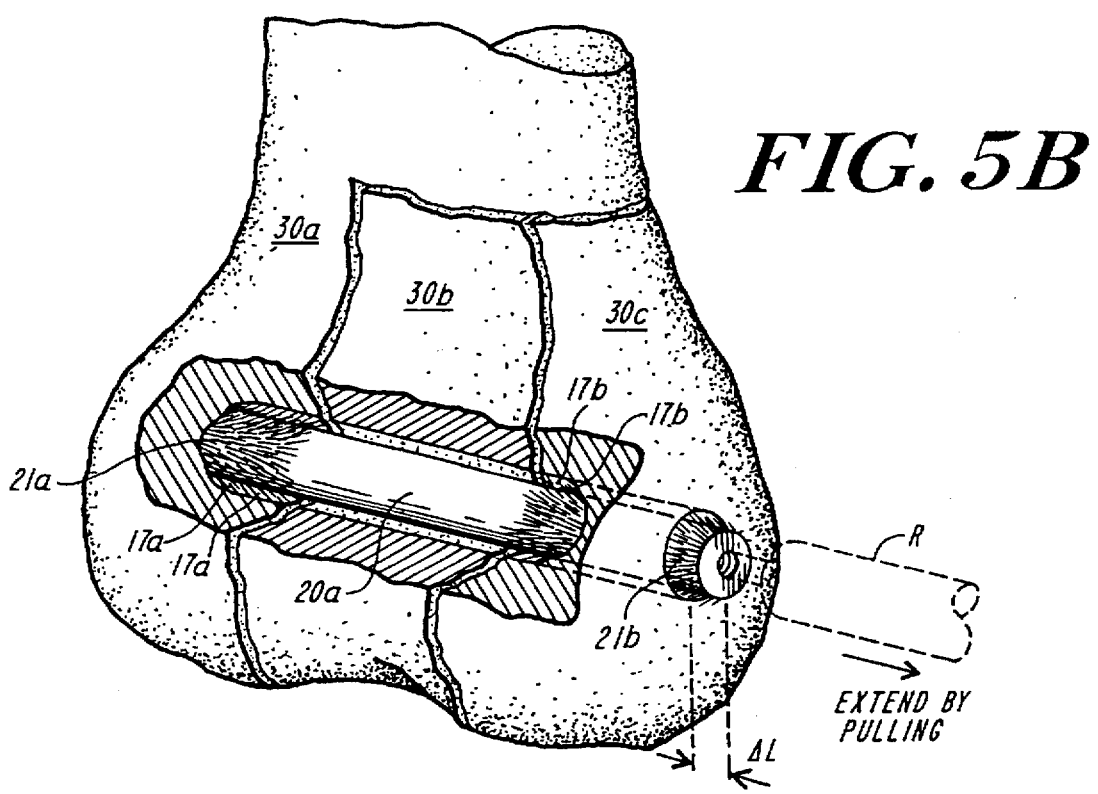
Figure 5C:
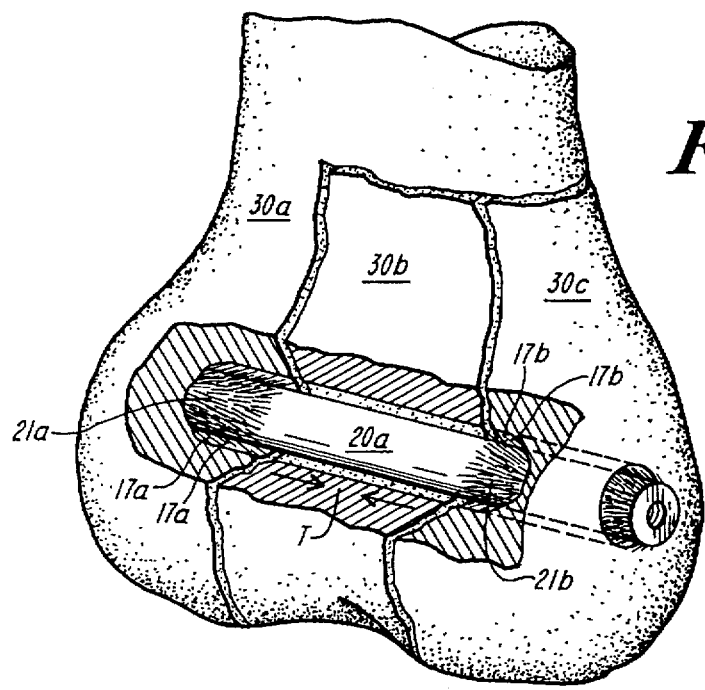

In addition to providing an asymmetric gripping force that allows easy insertion, yet resists removal, the bone pin of FIG. 5 may be used to provide a tensile loading of the reassembled bone. According to this aspect of the invention the bone pin 20a is fabricated of a stretchable material or with a stretchable central portion such that when pulled at one end, the pin elongates. As shown in FIGS. 5A–5C, initial assembly of the bone fragments on the pin results in a reconstruction of the fracture with the pin 20a in a tension free resting state. The outer end of the pin 20a is then pulled, e.g. by a threaded rod R removably attached to the pin to place the pin under tension and extend its length slightly by ΔL (FIG. 5B). The microtextured gripping teeth then grip their respective bone fragments in this pin-elongated position, so that the rod R may be removed while the pin remains held in its elongated state. Thereafter, the tension "T" of the pin exerts a compressive load against the bone fragments further enhancing bone healing growth (FIG. 5C). Instead of forming the pin of an extensible material, the pin may be mechanically assembled with an elastic middle portion such as a coil spring, to provide tension when extended. In a similar manner, a bone screw may be provided with an elastically-deformable body such that tightening results in locking the screw in a torsioned state that applies a continuing low level strain to the surrounding bone. Here, rather than axially compressing fragments together, the primary operative effect is to stimulate bone growth about the screw.

Figure 6:
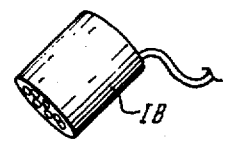
FIG. 6 illustrates fabrication of the embodiment of FIG. 5.
Figure 6:
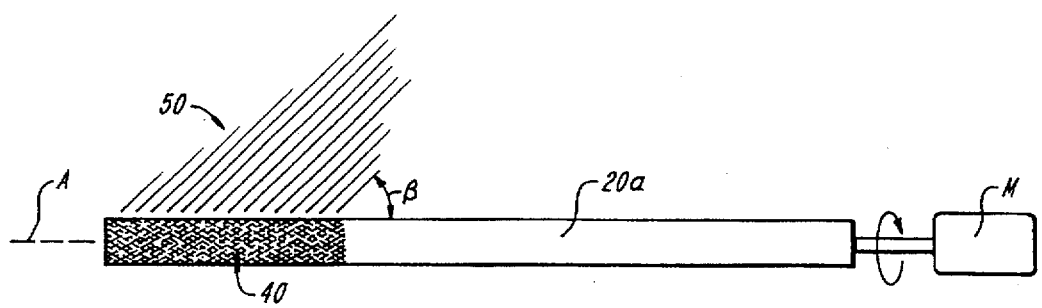

FIG. 6 illustrates the formation of one set of surface features 17. As illustrated therein, for manufacture the fixation device 20a is rotated about its axis by a turning motor M, while an ion beam IB is aimed at an acute angle β with respect to the pin axis "A" and aiming a stream of ions 50 toward the end of the pin optionally with a grid or reticulated pattern mask 40 which defines the column features so as to leave free ends of the microcolumns pointing inward toward the center of the pin. In a second treatment step the pin is turned around and the ion beam then irradiates toward the second end of the pin to produce a set of microcolumns having the opposite orientation. Thus, each set of microcolumns is anchored at its outer end in a region near the end of the pin, and points inwardly towards the center of the pin. The microcolumns thus resist motion of bone outwardly toward the end of the pin near either end.

In addition to bone screws and bone pins, other fixation devices such as eye hooks having a screw base and useful for attaching ligaments or the like to a site on a bone, and fixation devices such as staples, screw anchors and other known items of bone hardware may be given a macrotexture in accordance with the present invention to enhance their fixation. Textures of the foregoing types are advantageously applied to threads, prongs or gripping teeth of screw anchors, surfaces of pins, and legs of wire-like fasteners such as staples, and may be directional or anisotropic, depending upon the nature of the gripping forces desired. Engaging surfaces of other fastener components may similarly be provided with a texture in accordance with the present invention as illustrated by the designation t in FIG. 8. In addition to directed sputtering by ion beam bombardment, sputter-etching may be used to advantage for texturing the surface of polymers wherein the treating particles are a reactive material such as atomic oxygen.

Furthermore, in addition to the particular macrotextures described herein, other small or directional microtextures achievable by processes known in the art are also contemplated for application to fixation devices in accordance with the invention described herein. In addition, the invention contemplates new forms of fixation device, wherein rather than a large structural element mating with a bone directly, two metallic elements are provided, one a more or less conventionally shaped bone fixation device, and the other a metallic shim or liner having a surface texture which engages that of the fixation device. Thus, for example, a screw anchor, a metal band or a collar having a directional surface roughness as described above may be fastened to a bone for engagement with a mating metal surface in contact therewith. In this case, a relatively large area textured surface is attached to the bone and the fixation device then engages this metal surface with its own countervailing directional texture. This provides an extremely secure and non-wearing fixation of the two parts. Such an arrangement is illustrated in FIG. 7, wherein a textured plate 60 is fastened on a surface of a bone, and an external collar or plate 65 having a textured inner surface 66 is then strapped into engagement with the plate 60. This manner of mounting avoids the problem of creating excessive stresses in the bone on engagement surfaces and also prevents wear of mating surfaces since the matching tooth pattern on the metal part enables a precise and non-shifting engagement of the opposed textured surfaces of metal parts which may engage without creating debris that would otherwise clog the single features.

This completes a description of basic embodiments of the invention and the principles thereof. In general, the degree of microtexture is such that the features are much smaller than those conventionally found useful for enhancing trabecular bone growth or bone regeneration, and may extend for a distance of several micrometers to several hundred micrometers in a regular pattern or array which is adapted to smooth the mechanical engagement properties of the insertion device and enhance their grip against shifting or loosening. The invention being thus described, further variations and modifications thereof will occur to those skilled in the art, and all such variations and modifications are intended to be within the scope of the present invention, as defined by the claims set forth below.

We claim:

1. An implantable fixation device for providing tissue fixation, said device having a fixation body which bears a load along a load direction, and a tissue engaging surface effective to transfer load from tissue in contact with the tissue engaging surface to the fixation body, said tissue engaging surface having a plurality of protruding microfeatures effective to directly contact the tissue and being oriented to provide a first resistance to movement along one direction which is greater than a second resistance to movement along an opposite direction.

2. A fixation device according to claim 1, wherein the different directions include a direction of insertion and a direction of removal of the device, and the microfeatures increase gripping engagement in the direction of removal.

3. A fixation device according to claim 1, wherein the different directions include a direction of insertion and the protruding microfeatures reduce gripping engagement in the direction of insertion.

4. A fixation device according to claim 1, wherein the microfeatures are oriented to increase gripping engagement along a direction perpendicular to a load direction.

5. A fixation device according to claim 1, wherein said plurality of microfeatures include plural substantially identically-shaped microfeatures arranged in a regular array on said engaging surface.

6. A fixation device according to claim 5, the fixation body having said engaging surface adapted for engaging a bone to securely fix the body therein, wherein the engaging surface has a patterned microtexture of surface roughness which deforms under load to mechanically enhance gripping engagement of the surface installed in the bone.

7. A fixation device according to claim 6, wherein the surface roughness includes a plurality of deflectable microbeams having free ends oriented away from a direction of insertion of said fixation device.

8. A fixation device according to claim 6, wherein the surface roughness includes a pattern of asymmetrically shaped ridges formed in said device.

9. A fixation device according to claim 6, wherein the surface roughness comprises a plurality of microbumps having a height less than half a millimeter.

10. A fixation device according to claim 6, where the engaging surface includes a screw thread surface and the patterned microtexture is formed on the screw thread surface.

11. A fixation device according to claim 6, wherein the fixation device is a pin and the surface roughness is formed on the circumference of the pin.

12. A fixation device according to claim 11, wherein the surface roughness is axially anisotropic to prevent motion of bone off either end of the pin.

13. A fixation device according to claim 11, wherein the surface roughness has a directional characteristic and is formed in two regions with opposite senses.

14. A fixation device according to claim 6, wherein the surface roughness is formed by ion beam radiation as a steady state pattern of protrusions.

15. A fixation device according to claim 6, wherein the surface roughness is formed by ion beam radiation through a pattern.

16. A fixation device according to claim 6 wherein said fixation body is elastically extensible so that said body is secured under tension when the body is extended and said engaging surface grips a bone.

17. A fixation device according to claim 6, wherein said fixation device is mechanically active for applying load or stress to the bone.

* * * * *